United States Patent
Mosler et al.

(10) Patent No.: US 8,075,508 B2
(45) Date of Patent: Dec. 13, 2011

(54) SHOE RELEASING ASSEMBLY FOR AN ORTHOSIS

(75) Inventors: Theodore J. Mosler, Raleigh, NC (US); Todd M. Korogi, Raleigh, NC (US); Andrew J. DiMeo, Raleigh, NC (US); Scott P. Jarnagin, Seattle, WA (US)

(73) Assignee: Dotted Intellectual Property, LLC, Research Triangle Park, NC (US)

( * ) Notice: Subject to any disclaimer, the term of this patent is extended or adjusted under 35 U.S.C. 154(b) by 855 days.

(21) Appl. No.: 12/089,499

(22) PCT Filed: Oct. 7, 2006

(86) PCT No.: PCT/US2006/039362
§ 371 (c)(1),
(2), (4) Date: Apr. 7, 2008

(87) PCT Pub. No.: WO2007/044650
PCT Pub. Date: Apr. 19, 2007

(65) Prior Publication Data
US 2008/0214975 A1    Sep. 4, 2008

Related U.S. Application Data

(60) Provisional application No. 60/724,945, filed on Oct. 8, 2005.

(51) Int. Cl.
*A61F 5/00* (2006.01)
*A61F 5/24* (2006.01)
*A61F 5/14* (2006.01)
*A44B 1/04* (2006.01)
*A43B 23/28* (2006.01)

(52) U.S. Cl. ............. 602/29; 128/95.1; 24/168; 36/140; 36/58.5

(58) Field of Classification Search ............... 602/24, 602/28, 29, 1, 5, 6, 8, 9, 10, 11, 12, 23, 35; 36/140, 58.5, 142, 143, 144, 145; 24/168, 24/170; 280/624
See application file for complete search history.

(56) References Cited

U.S. PATENT DOCUMENTS 4,088,129 A    5/1978  DiGiulio
(Continued)

OTHER PUBLICATIONS

International Search Report, corresponding to International Patent Application No. PCT/US06/39362, dated Apr. 3, 2007.

*Primary Examiner* — Patricia Bianco
*Assistant Examiner* — Tarla Patel
(74) *Attorney, Agent, or Firm* — Moore & Van Allen, PLLC; Christopher J. Knors

(57) ABSTRACT

A shoe releasing assembly for use with an orthotic bar or splint is disclosed. The shoe releasing assembly comprises a bar attachment member securable to a bar or splint, a shoe attachment member securable to the sole of a shoe, and latching means to secure the bar and shoe members. The bar attachment member comprises a base, a wall section at least partially surrounding the base. The shoe attachment member comprises a shoe attachment base, a shoe attachment wall section at least partially surrounding the shoe attachment base. When one of the attachment members comprises a wall section defining a recess, the corresponding member comprises a wall section having a shape conforming to the recess for vertically inclined insertion. Latching means are provided for receiving, securing, and disengaging the shoe attachment member to the bar attachment member. Methods of treating foot disorders using the assembly are also disclosed.

23 Claims, 15 Drawing Sheets

U.S. PATENT DOCUMENTS

| | | |
|---|---|---|
| 4,157,876 A | 6/1979 | DiGiulio |
| 4,760,850 A | 8/1988 | Phillips et al. |
| 5,382,225 A | 1/1995 | Sutcliffe |
| 5,470,310 A | 11/1995 | Sutcliffe |
| 6,428,493 B1 | 8/2002 | Pior et al. |
| 6,432,073 B2 | 8/2002 | Pior et al. |
| 7,267,657 B1 * | 9/2007 | Mitchell ............... 602/29 |
| 2007/0073206 A1 | 3/2007 | Hatton et al. |

* cited by examiner

SHOE RELEASING ASSEMBLY FOR AN ORTHOSIS

CROSS-REFERENCE TO RELATED APPLICATIONS

The present application is a National Stage application of International Application No.: PCT/US2006/039362 filed on Oct. 7, 2006, which claims the benefit of U.S. Provisional Patent Application No.: 60/724,945 filed on Oct. 8, 2005, the contents of both of which are hereby incorporated by reference herein in their entireties.

FIELD

This invention relates to quick release shoe assemblies suitable for use in orthotic devices and procedures utilizing a bar or Dennis Browne splint.

BACKGROUND

Club foot is a serious birth defect found worldwide and effective treatment may take up to 3 years. This disorder is treated in a variety of ways. One of the most clinically accepted and successful treatments, termed the Ponseti Method, requires incremental readjustment of the feet with castings, followed by using a brace or other stabilizing devices to maintain abduction of the foot. Current stabilizing devices include a Denis Browne splint that is secured to special shoes that are worn by children afflicted with this condition and other related conditions of the foot and legs. The Denis Browne splint or "night splint" must often times be worn all night and throughout the day. While it has been proven to be effective in realigning children's feet and helping them gain a normal level of functionality, the device is somewhat cumbersome and inconvenient to use. As such, non-compliance with the treatment may result.

For example, many caregivers have reported that the current Denis Browne Splint is difficult to put on and is problematic when performing tasks such as changing diapers, putting the child in a car seat, putting the child to sleep, and changing clothes. While performing these tasks the child often experiences discomfort, making the removal and reattachment of the splint more taxing to the caregiver as well. As a result, caregivers tend to allow the child to forego using the splint during these tasks due to these inconveniences and discomforts, thus deviating from the prescribed regimen. Subsequently the duration of the therapy must be prolonged or the child may relapse or regress, restricting the child from the full benefit of the treatment.

A typical Denis Browne splint comprises a rigid bar adapted to be connected between the feet of a patient, and means at either end of the bar for attachment to the patient's feet, maintaining the feet in the desired relationship to each other. The rigid bar may be attached to the patient's shoes by various means. In some instances, plates are permanently attached to the bar and attached to the soles of the shoes by screws. The system of bars and plates requires maintaining the desired adjustment while the screws which attach the plates to the bar are tightened to the sole of the shoe with tools. This may make accurate adjustment somewhat difficult. Consequently, once the adjustment is made, it is usually maintained, and the removal and replacement of the splint requires the removal and replacement of the patient's feet from the shoes while the shoes stay attached to the splint.

Another system for attachment of the bar to the patient's feet requires the use of clamps which clamp the sides of the sole of the shoe. The clamps may be detached from the shoes without disturbing the adjustment of the splint, but it is difficult to reattach the splint to the shoes in the exact relationship desired.

Another system for attachment of the bar to the patient's feet requires sliding engagement of clip means with a track formed by ribs in a shoe clip means, the shoe clip means being fixed to a articulated joint for releasable rigid attachment. Although the shoes may be attached to and detached from the splint by means of the clip means and shoe clips, it may be necessary to extend the patient's legs forward in order to insert the shoe clip means into the track of the clip means. This extension of the leg and foot may be difficult for the caregiver and uncomfortable for the patient. Moreover, the track assembly may not provide sufficient stability to the assembly which may result in excess play and rattle of the shoe and splint. As a result, non-compliance with a corrective foot orthotic treatment may result with the aforementioned systems.

Certain conditions of the lower extremities require the maintenance of either of plantar (toe down) or dorsi (toe up) flexion on one or both feet. The ordinary Denis Browne splints may not be capable of correcting such conditions, and while other devices exist for these conditions, using them in addition to the Denis Browne splint is difficult. Consequently, it is difficult to correct some of the more complex deformities.

SUMMARY

To remedy these problems, a shoe releasing assembly is herein described adaptable to a Denis Browne Splint that comprises a quick release mechanism for detaching the splint from the shoes. By incorporating a snap-fit locking mechanism with a convenient release tab underneath the shoe a caregiver may quickly and easily remove and reapply the Denis Browne splint. By amending the standard Denis Browne Splint the treatment of club foot could be much less traumatic for both the child and the caregiver. Consequently, the caregivers should be much more likely to follow the prescribed regimen, which should translate into more rapid and effective treatment of club foot using the Denis Browne Splint or similar device.

A quick releasing shoe assembly providing a practical solution to one or more of the above-mentioned problems with prior art braces, and an assembly which is applicable to use in combination with a wide variety of lower extremity conditions, which is of uniform design, and which is simple, easily manufacturable and relatively low in cost, thereby resulting in a decreased cost to the patient's family is provided.

In one embodiment, a shoe releasing assembly is provided comprising a bar attachment member securable to a bar or splint. The bar attachment member comprises a base having a forward end and a rearward end, a wall section at least partially surrounding the base and defining a recess, and at least one releasing member integral to the bar attachment member and positioned within the recess or the wall section, the releasing member comprising at least one retaining element. The assembly also comprises a shoe attachment member securable to the sole of a shoe, the shoe attachment member comprising a shoe attachment base having a heel end and a toe end, a shoe attachment wall section at least partially surrounding the shoe attachment base and having a shape conforming to the recess of the bar attachment member for vertically inclined insertion into the recess of the bar attachment member, and an integral locking element adjacent the shoe attachment wall for releasably engaging the retaining element. The releasing member provides for disengagement of the retaining element from the integral locking element.

In another embodiment, a shoe releasing assembly is provided comprising a bar attachment member securable to a bar or splint. The bar attachment member comprises a base having a forward end and a rearward end, a wall section at least partially surrounding the base, and an integral locking element adjacent the wall section. The assembly also comprises a shoe attachment member securable to the sole of a shoe. The shoe attachment member comprises a shoe attachment base having a heel end and a toe end, a shoe attachment wall section at least partially surrounding the shoe attachment base and defining a recess, the recess having a shape conforming to the wall section of the bar attachment member for vertically inclined insertion of the wall section of the bar attachment member into the recess of the shoe attachment member. The assembly further comprises at least one releasing member integral to the shoe attachment member positioned within the recess or shoe attachment wall section, the releasing member comprising a retaining element for releasably engaging with the locking element. The releasing member provides for disengagement of the retaining element from the locking element.

In another embodiment, a shoe releasing assembly is provided comprising a bar attachment member securable to a bar or splint. The bar attachment member comprises a base, and a wall section at least partially surrounding the base and defining a recess. The assembly also comprises a shoe attachment member securable to the sole of a shoe, the shoe attachment member comprising a shoe attachment base and a shoe attachment wall section at least partially surrounding the shoe attachment base and having a shape conforming to the recess of the bar attachment member for vertically inclined insertion into the recess of the bar attachment member. The assembly further comprises latching means for cooperatively receiving and releasably securing the shoe attachment member to the bar attachment member, and for providing disengagement of the shoe attachment member from the bar attachment member.

In another embodiment, a shoe releasing assembly is provided comprising a bar attachment member securable to a bar or splint. The bar attachment member comprises a base and a wall section at least partially surrounding the base. The assembly also comprises a shoe attachment member securable to the sole of a shoe, the shoe attachment member comprising a shoe attachment base and a shoe attachment wall section at least partially surrounding the shoe attachment base and defining a recess, the recess having a shape conforming to the wall section of the bar attachment member for vertically inclined insertion of the bar attachment member. The assembly further comprises latching means for cooperatively receiving and releasably securing the shoe attachment member to the bar attachment member, and for providing disengagement of the shoe attachment member from the bar attachment member.

In another embodiment, a method for treating a foot disorder in a subject in need thereof is provided. The method comprises providing a bar or splint comprising a pair of securing plates and securing a bar attachment member to each of the pair of securing plates. The bar attachment member comprises a base having a first end and a second end and a wall section, the wall section at least partially surrounding the base and defining a recess. The method also comprises providing a shoe, securing a shoe attachment member to the sole of the shoe. The shoe attachment member comprises a shape conforming to the recess of the bar attachment member for vertically inclined insertion into the recess of the bar attachment member. The method further comprises securing the shoe attachment member to the bar attachment member using latching means for cooperatively receiving and releasably securing the shoe attachment member to the bar attachment member, and for providing disengagement of the shoe attachment member from the bar attachment member.

Other embodiments and equivalents thereof will be apparent from the following detailed description when read in conjunction with the drawings.

DETAILED DESCRIPTION

Figure 1:
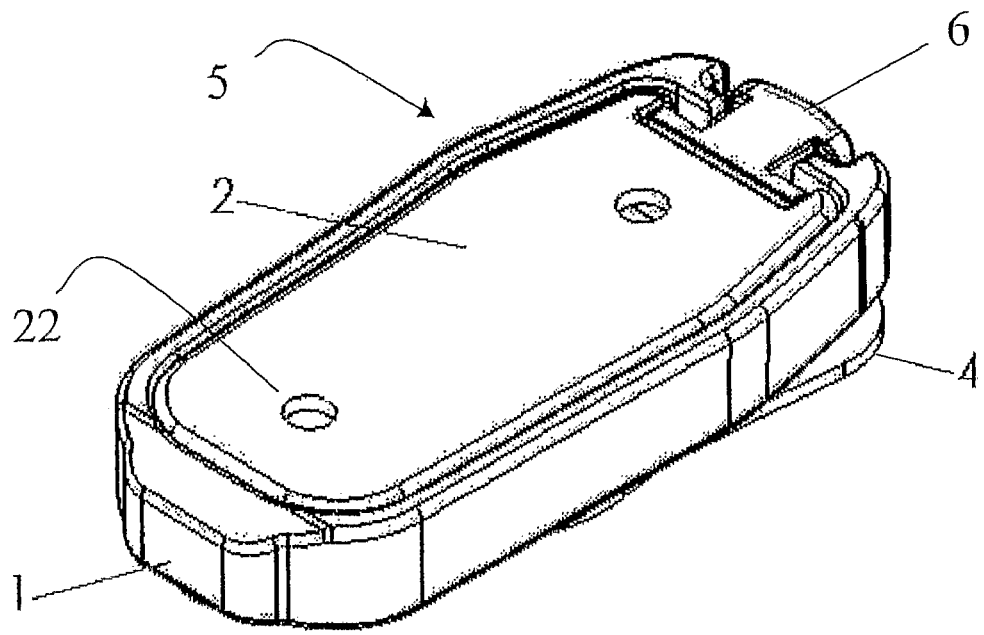
FIG. 1 is a perspective assembled view of one embodiment of the shoe releasing assembly.

The present invention relates to quick releasing shoe assemblies adapted for use with devices generally known as "Denis Browne Splints" or "night splints" or "abduction braces", this term denoting devices adapted to be connected between the patient's feet and which hold the feet at a fixed distance from each other while performing a corrective function.

The shoe releasing assembly generally comprises a bar attachment member securable to a bar or splint, a shoe attachment member securable to the sole of a shoe, and latching means to secure the bar and shoe members. The bar attachment member comprises a base, a wall section at least partially surrounding the base. The shoe attachment member comprises a shoe attachment base, a shoe attachment wall section at least partially surrounding the shoe attachment base. Whereas when one of the attachment members comprises a wall section defining a recess the corresponding member comprises a wall section having a shape conforming to the recess for vertically inclined insertion into the recess of the corresponding attachment member.

The latching means provide for cooperatively receiving and releasably securing the shoe attachment member to the bar attachment member, and for providing disengagement of the shoe attachment member from the bar attachment member.

Referring now to the drawings, various illustrative embodiments will be described. FIGS. 1 through 4 generally depicts a shoe releasing assembly embodiment. Assembly 5 which includes a bar attachment member 1 securable to a plate 4 (or 50) of a bar or splint and shoe attachment member 2 securable to a shoe. Throughholes 22 on shoe attachment member provide attachment means for attachment to a shoe or other readily attachable platform. Release member 6, shown integral with bar attachment member 1 comprises means for releasing the shoe attachment member from the bar attachment member as explained below. Various latch means and click and lock/release structures are suitable as releasing member as shown as is known in the art.

Figure 2:
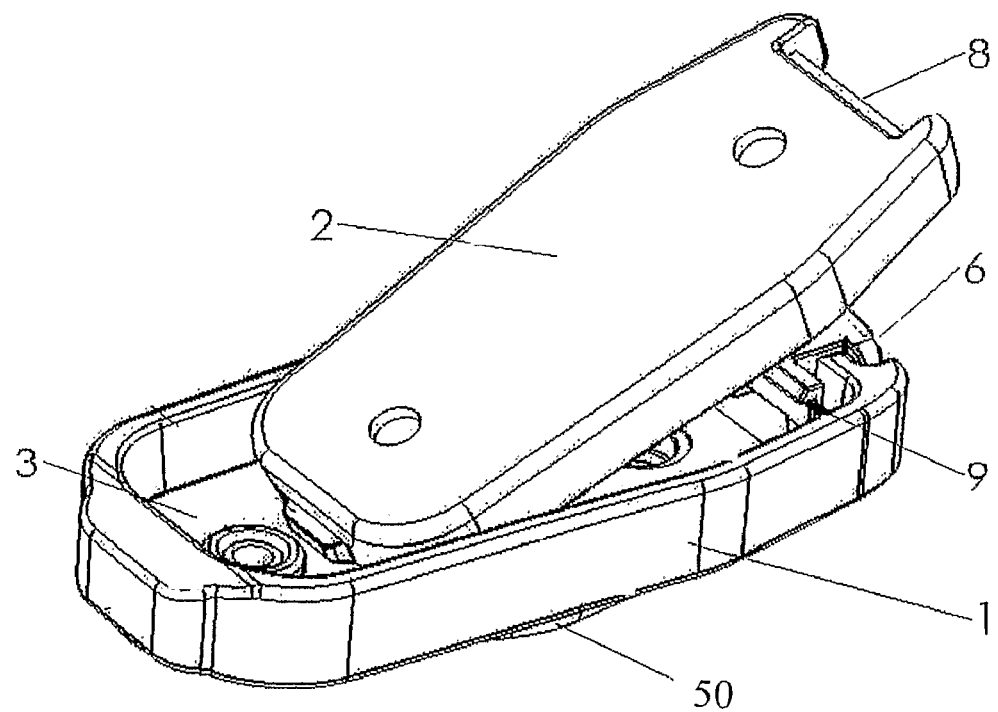
FIG. 2 is a perspective unassembled view of the shoe releasing assembly of FIG. 1.

FIG. 2 depicts the assembly in a partially vertically inclined assembled state. Locking element 8 of the shoe attachment member, engages releasing member 6 of the bar attachment member and is held by retaining element 9 to releasably secure the shoe attachment member to the bar attachment member.

Figure 3:
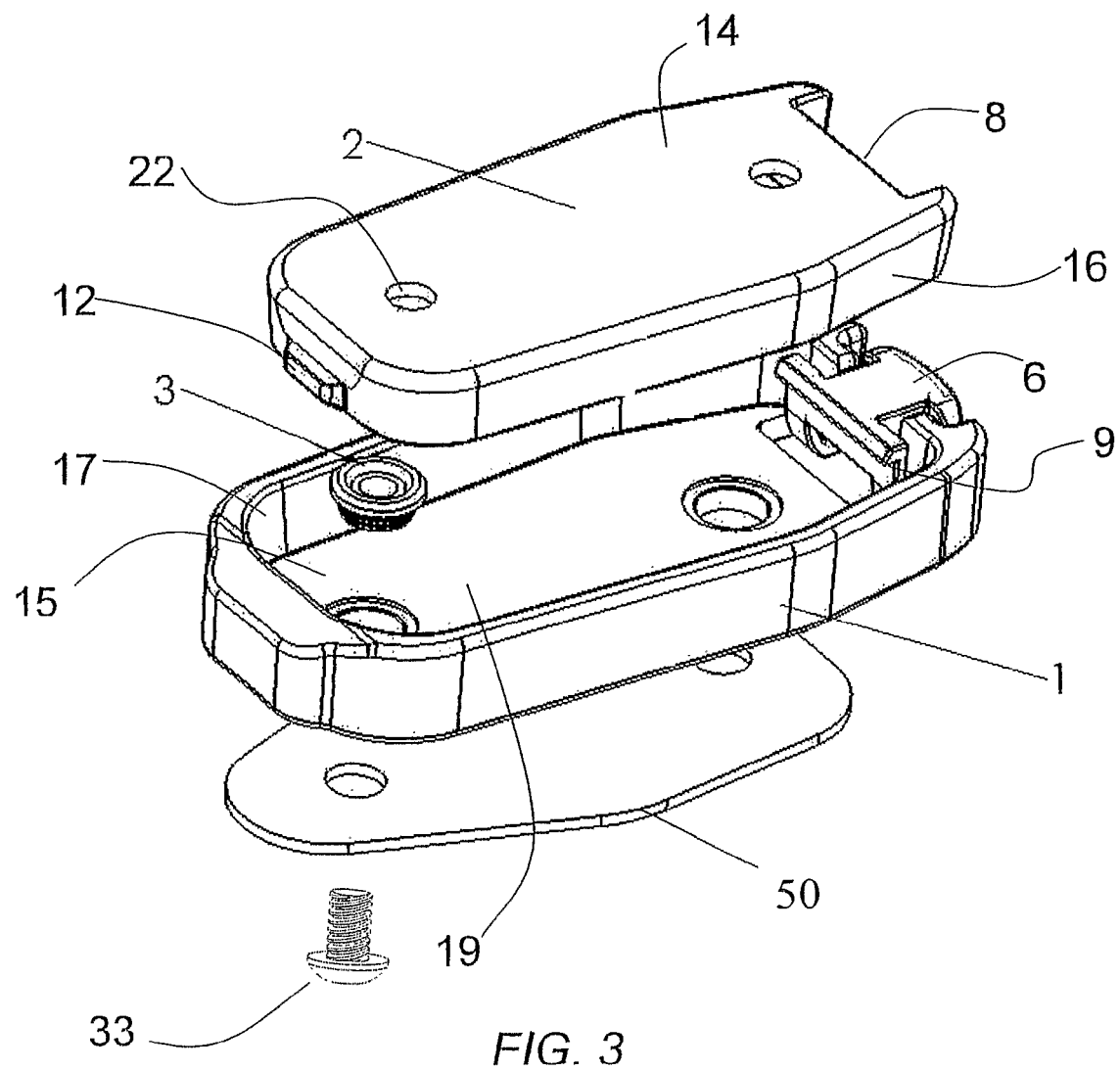
FIG. 3 is an exploded perspective view of the assembly in FIG. 2.
Figure 4:
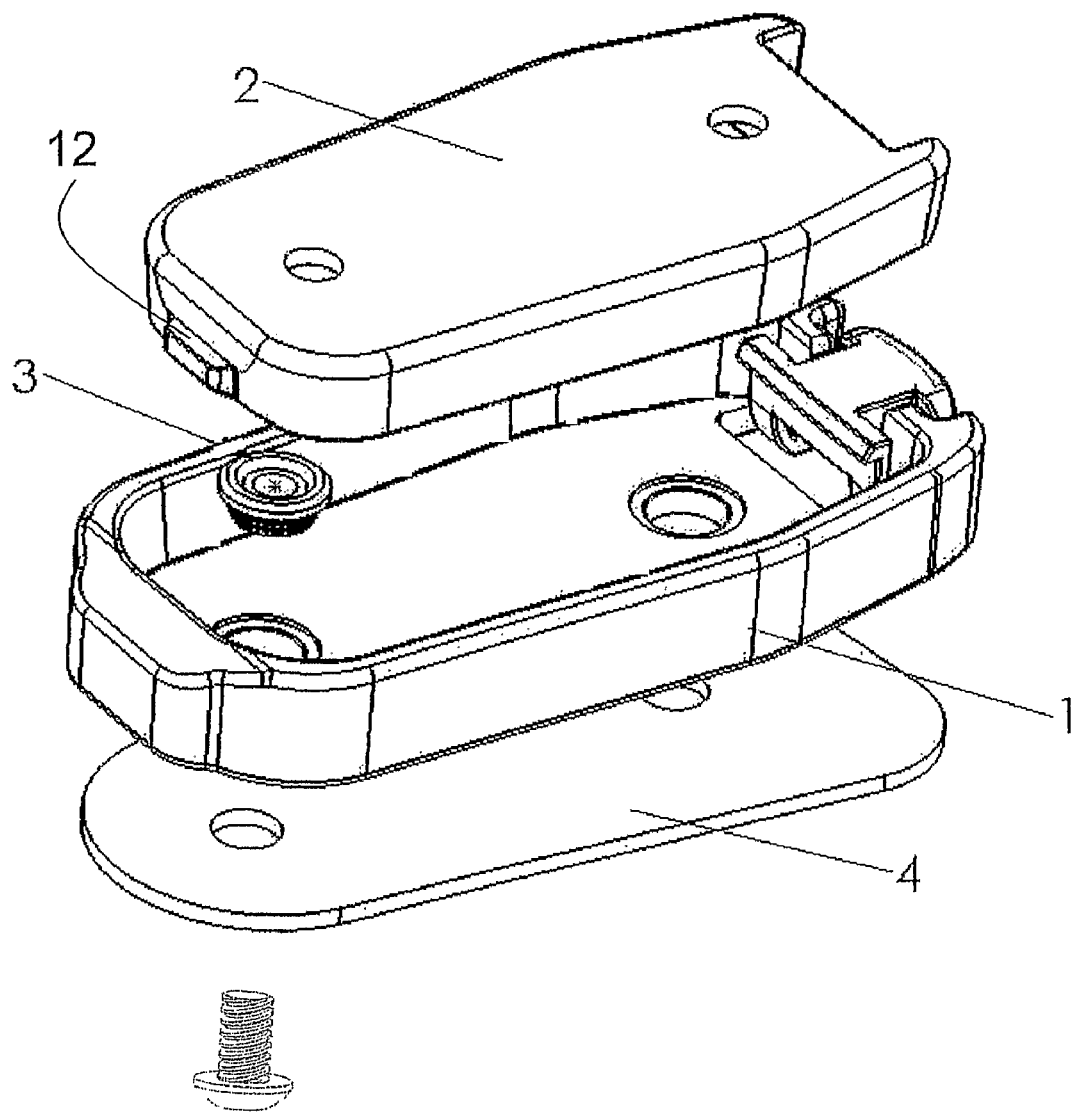
FIG. 4 is an exploded perspective view of the assembly in FIG. 1.
Figure 5:
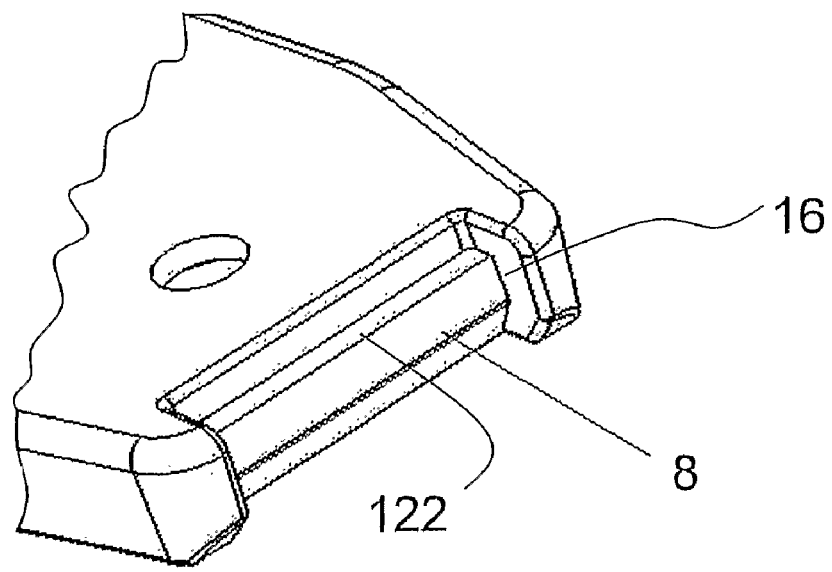
FIG. 5 is partial perspective view of a shoe attachment member of FIG. 1.

FIG. 3 depicts an exploded view of the assembly of FIG. 1. Bar attachment member 1 comprises base 15 which is at least partially surrounded by wall 17 providing a recess 19. Shoe attachment member 2 comprises shoe attachment member base 14 and shoe attachment member wall section 16 which at least partially surrounds shoe attachment member base 14. The shoe attachment wall section may be hollowed out or may be solid as desired. The shoe attachment member wall section 16 is sized to complement the recess 19. Threaded insert element 3 secures bar attachment member 1 to plate 4 via screw element 33. Protrusion element 12 of shoe attachment member 2 is positioned on shoe attachment member base 14 opposite locking element 8.

Figure 6:
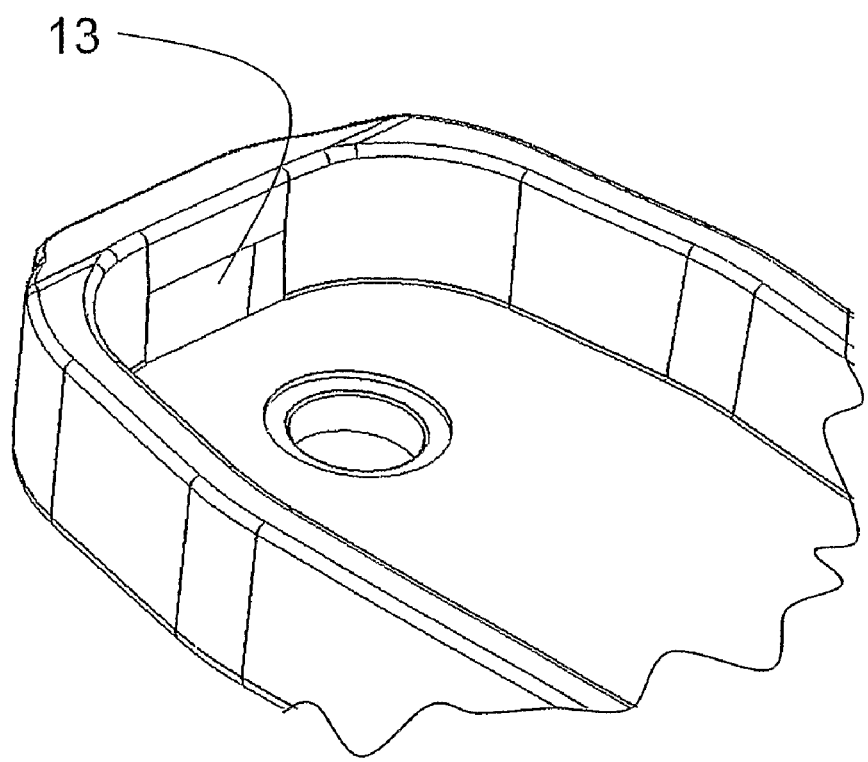
FIG. 6 is a partial perspective view of a bar attachment member of FIG. 1.
Figure 7:
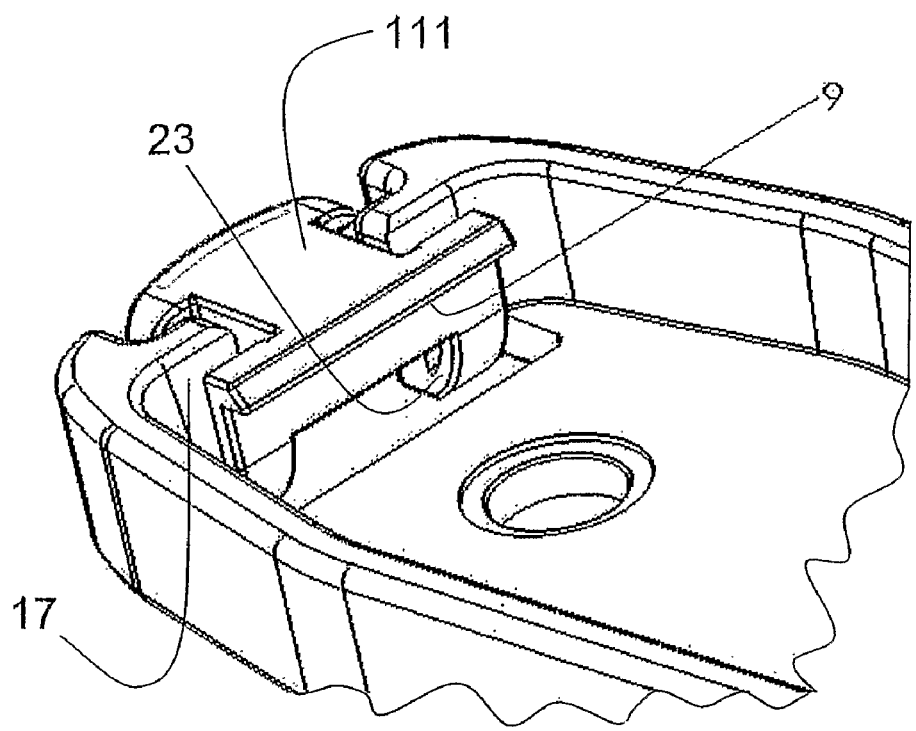
FIG. 7 is a partial perspective view of a bar attachment member of FIG. 1.
Figure 8:
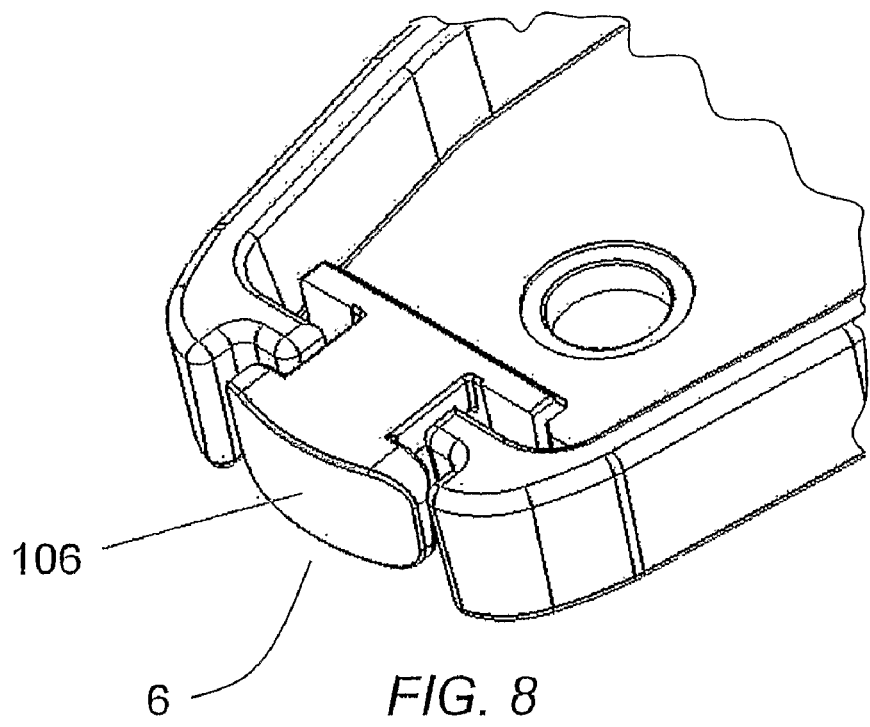
FIG. 8 is partial perspective view of a bar attachment member of FIG. 1.

Retaining element 9 is correspondingly positioned on the bar attachment member to receive locking element 8 during engagement. Securing element 13 (FIG. 6) adjacent base 15 and wall 17 is correspondingly positioned to receive protrusion element 12 of shoe attachment member 2. The retaining/locking element and protrusion/securing elements may be of any suitable structure, size and shape as is known in the art.

Referring now to FIGS. 5 through 9, locking element 8 includes recessed ledge 122 positioned adjacent to shoe attachment member wall section 16 providing engagement with resilient, flexible cantilever element 23 and retaining element 9 of rearwardly positioned release member 6. Flexible cantilever element 23 of retaining element 9 adjoins wall section 17 and retaining element 9 extends rearwardly providing platform 111 that terminates with actuator 106. During engagement of the shoe attachment member with the bar attachment member, securing element 13 receives protruding element 12 followed by contact of locking element 8 with retaining element 9 displacing cantilever element 23 rearwardly to receive recessed edge 122 of locking element 8. Various other structures and mechanisms as are known in the art may provide the functionality of a snap-fit latching means, of which the cantilever element described above is an exemplary structure representing such a releasable snap-fit type latching means.

Upon full engagement, the recessed ledge is positioned below retaining element 9, which returns to essentially an initial position or one with slight forward tension on the cantilever element. The resiliency of the cantilever element urges retaining element 9 in the forward direction so that retaining element 9 is positioned on the recessed ledge 122 formed in locking element 8. This provides securing or latching means securing the shoe attachment member to the bar attachment member. Adjustment of the tension of cantilever element may provide for optimization of the engagement and disengagement properties of the assembly as needed. Retaining element 9 may be beveled as shown or may be any shape or size suitable to assist in receiving recessed ledge and in displacing cantilever 23.

Releasing member 6 is provided with an integral actuator 106, which extends outwardly from the body of bar attachment member 1 in a generally parallel relation to long axis of the base 15 and is attached to the cantilever element of the retaining element.

Protrusion element 12 is typically engaged with securing element 13 of bar attachment member by vertical inclined insertion of shoe attachment member 2 into bar attachment member 1 such that the protrusion element will engage the securing element and prevent or minimize rotation of the shoe attachment member during final engagement.

The individual locations of the releasing member and corresponding locking member may be reversed. The individual locations of the protrusion and corresponding securing elements may be reversed. In this manner, the shoe attachment member assembly may be inserted "heel-first" or "toe-first" into the bar attachment member as desired.

Moreover, the releasing member and securing elements as herein described may be alternatively positioned on the shoe attachment member while the corresponding locking and protrusion elements may be positioned on the bar attachment member as desired.

The assembly may provide for an audio indication of full engagement and securement of the assembly, for example, an audible click or snap.

Figure 9:
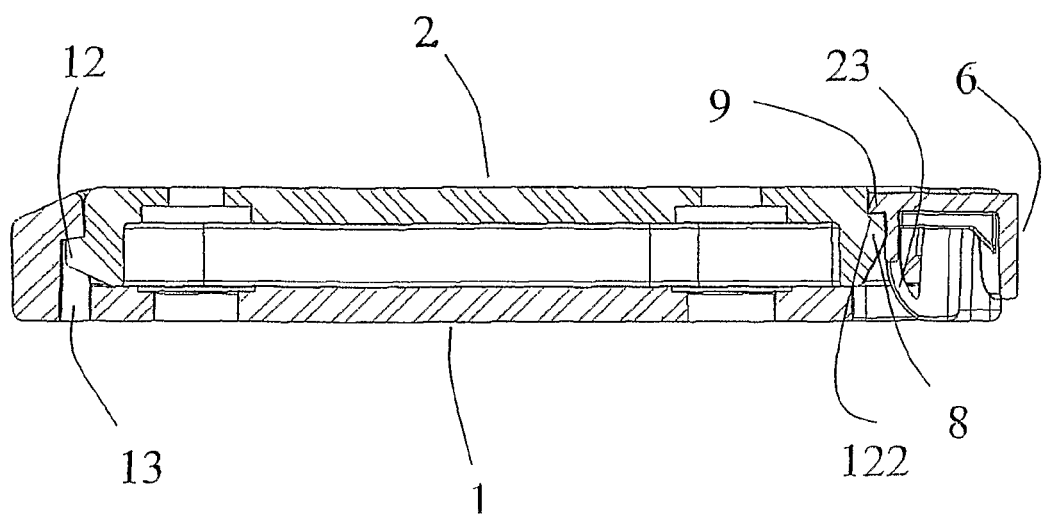
FIG. 9 is a sectioned elevation view of the embodiment in FIG. 1.

To disengage the shoe attachment member from the bar attachment member, the user activates the releasing member 6. Pulling rearwardly on actuator 106 of releasing member 6 translates retaining element 9 rearward from recessed ledge 122 and enables disengagement of an end of the shoe attachment member from the bar attachment member and subsequently the protrusion element from the securing element. A sectional view of the fully engaged shoe releasing assembly attachment members 1 and 2 with the engagement of locking/retaining elements and protrusion/securing elements is shown in FIG. 9.

Figure 10:
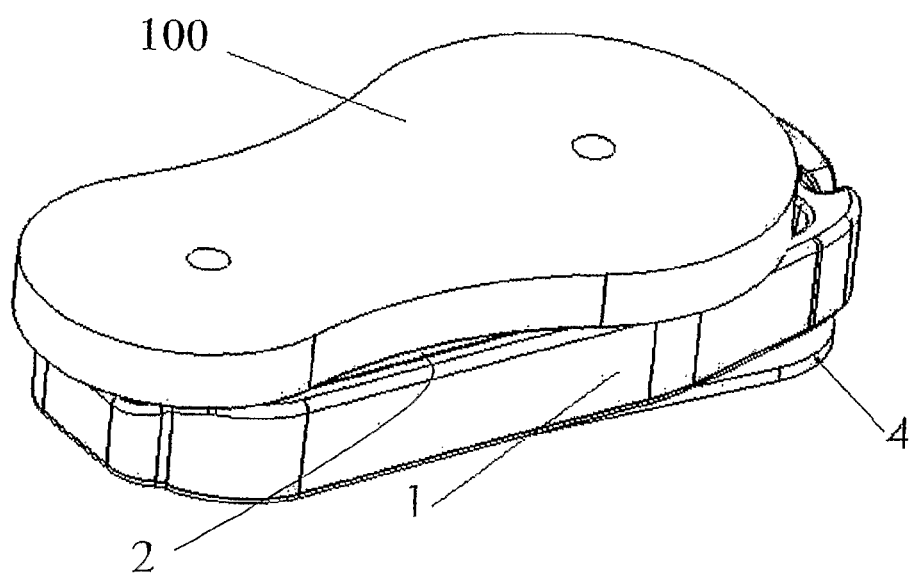
FIG. 10 is a perspective view of the assembled embodiment in FIG. 1 attached to the sole of a shoe.

As shown in FIG. 10, the shoe attachment member may be attached to the sole 100 of a shoe. The attachment may be achieved by the use of screws or a suitable adhesive. This may allow the shoe attachment member to be readily and easily applied to the sole of an ordinary infant's shoe without the use of tools or by the infant's caregiver. The shoe attachment member may be applied to the shoe by the orthopedist himself in his own office immediately prior to the initial adjustment of the splint. The shoe attachment member may be secured to the sole of the shoe by suitable screws or rivets via countersunk holes being provided in the shoe attachment member, for example.

Additional elements to assist the release of the shoe attachment member from the bar attachment member and/or to minimize or eliminate excess play or rattle in the fully engaged assembly are now described.

Figure 11:
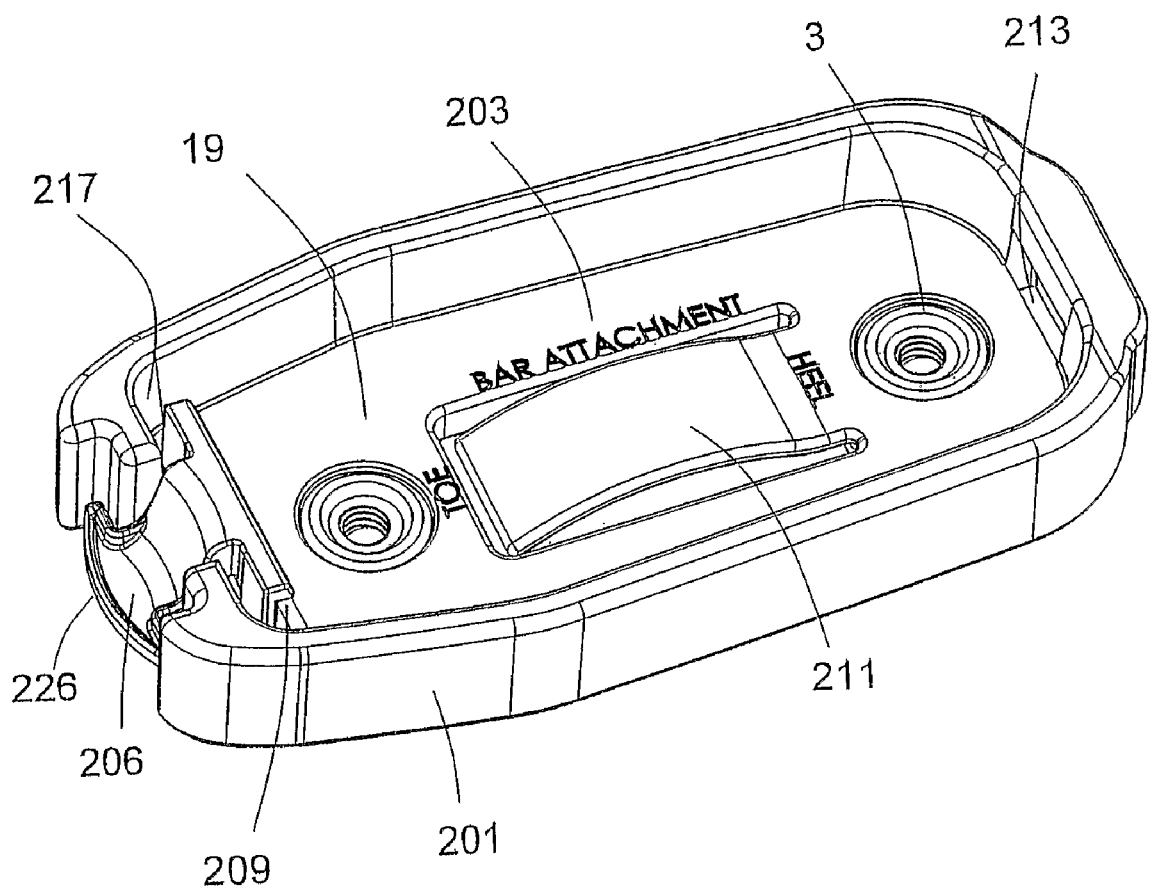
FIG. 11 is a perspective view of another bar attachment member embodiment.
Figure 12:
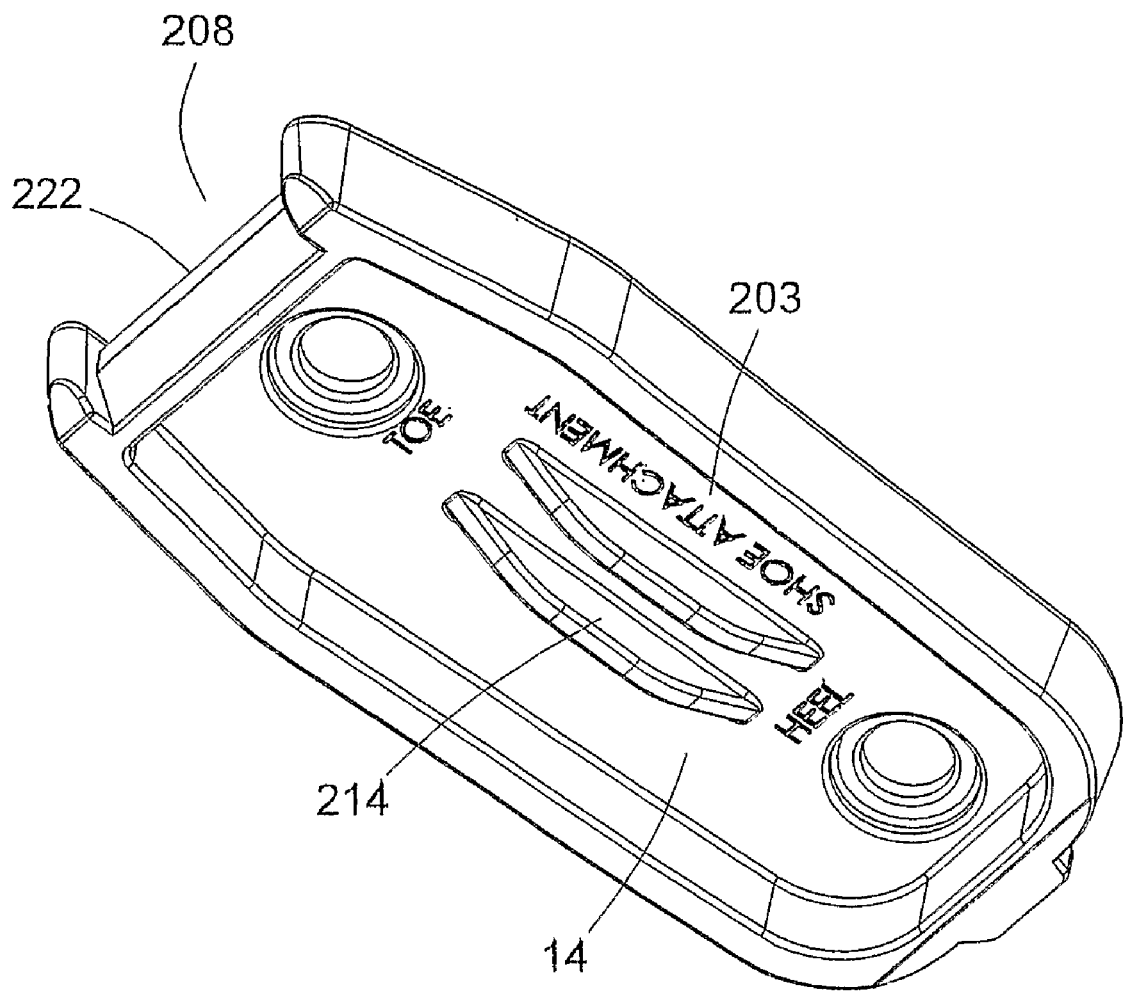
FIG. 12 is a perspective view of another shoe attachment member embodiment.
Figure 13:
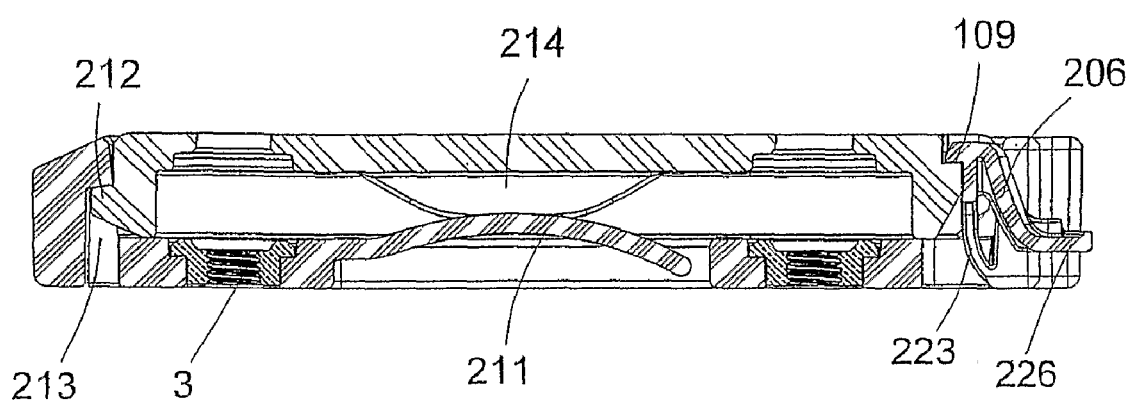
FIG. 13 is a sectioned elevation view of the assembled shoe releasing assembly of embodiments shown in FIGS. 12 and 13.

Referring now to FIGS. 11 through 13, interference element 214 positioned on the shoe attachment member base 14 interfere with deflector element 211 positioned in the recess 19 of bar attachment member 201. Deflector elements may be shaped as a protruding flange, tongue, arch, spring or other shape as desired. Upon engagement of the assembly interference element 214 interferes with deflector element to apply a load and thus minimize or eliminate play or rattle between the shoe attachment member and the bar attachment member. In addition, by deflecting deflector element 211 a stored force may be created that upon activation of the releasing member, the stored force may be released to assist in the disengagement of the assembly components. Design and optimization of the interference and deflector elements for these and other purposes is within the skill of one practicing in the art. Text indicia 20 may be added to aid the user in assembling the parts of the assembly. The overall shape of the shoe releasing assembly may also be wider at the toe end, and narrower at the heel end reflective of the shape of the foot to visually aid the user with the proper orientation for assembly. Thus, as described, the releasing member may provide for one-handed and/or quick releasing operation of the shoe assembly.

Referring again to FIGS. 11 through 13, alternate embodiments of the actuator of the shoe releasing assembly are described. Releasing member 206 is depicted having a tab and cantilever element as previously described with an alternate actuator 226. Actuator 226 extends downwardly along wall section 217 to enable the user to push the actuator and translate retaining element 209 rearward to release recess ledge 222 of the corresponding locking element 208. Such an actuator may be desirable, for example, when the releasing member is positioned on the shoe attachment member to allow access to and activation of activator 226 underneath a shoe.

Referring now to FIG. 13, a cross-sectional view of the assembled attachment member embodiments of FIGS. 11 and 12 is shown. Protrusion element 212 is shown engaged with securing element 213. Release member 206, cantilever element 223 and actuator 226 are shown. Deflector element 211 positioned between threaded inserts 30 is shown interfering with the interference element 214.

Figure 14:
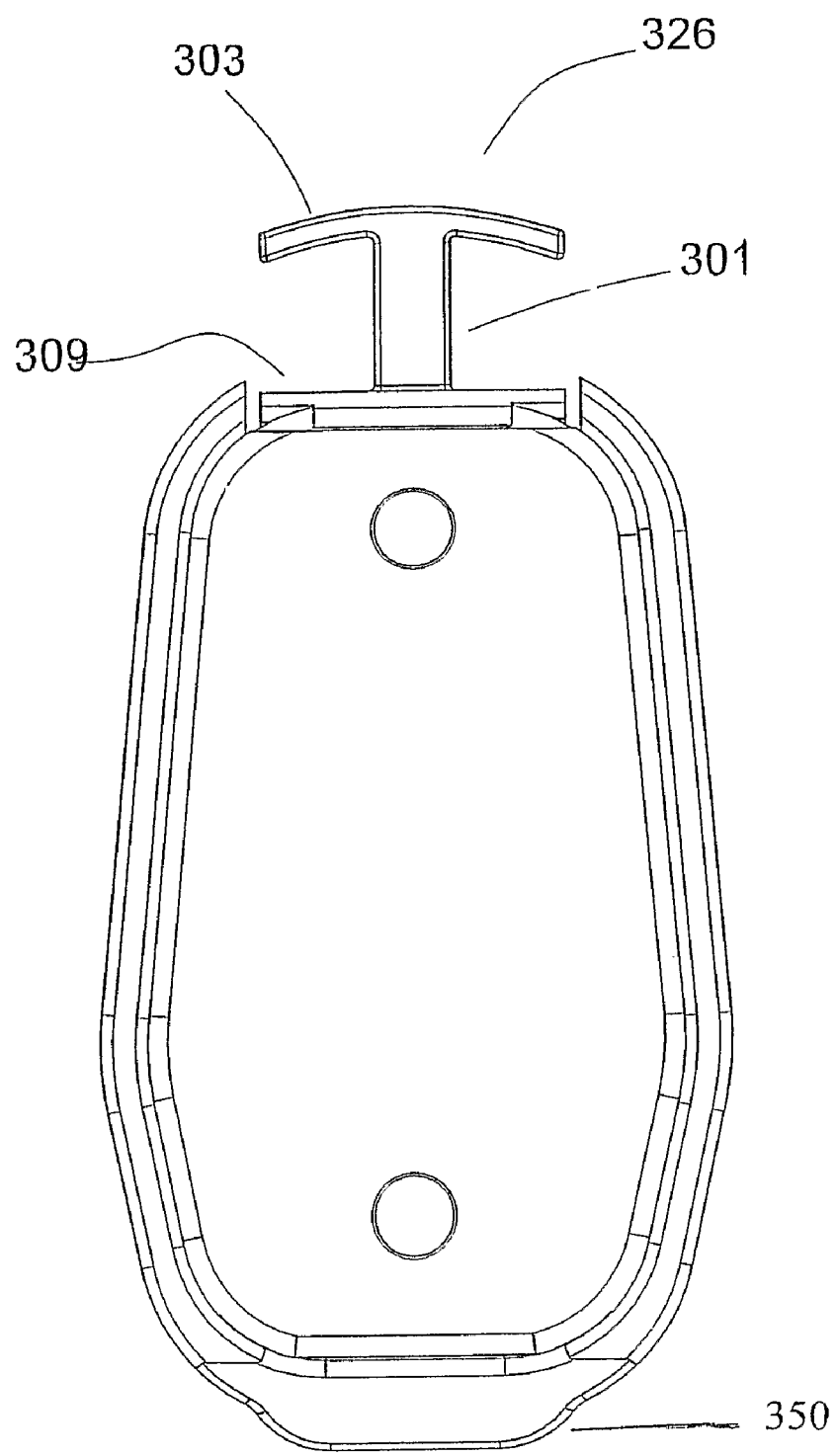
FIG. 14 is a top plan view of a bar attachment member embodiment.

FIG. 14 depicts alternate actuator 326, which extends from retaining element 309 by arm 301 and includes t-shaped terminus 303 for facile actuation by grasping with one or more fingers.

Figure 15:
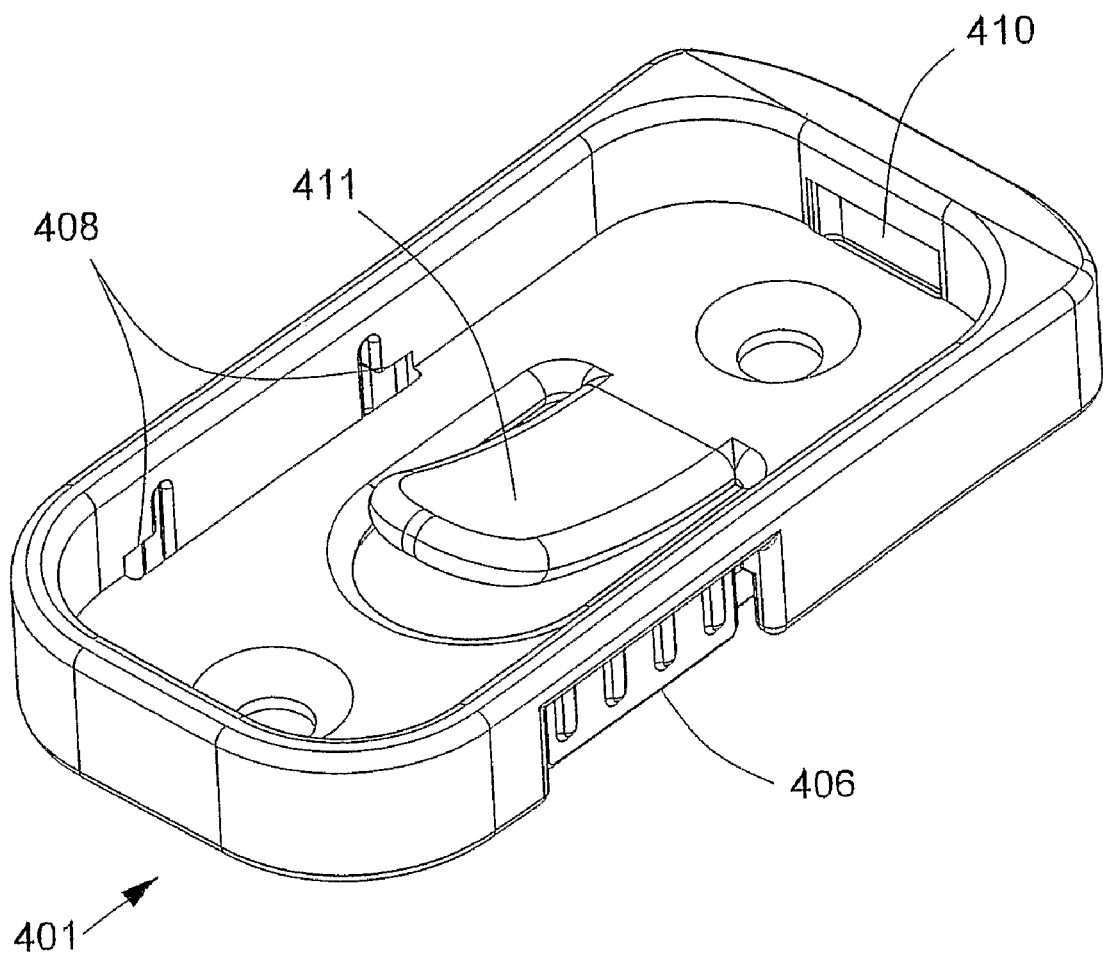
FIG. 15 is an perspective view of a bar attachment member embodiment.
Figure 16:
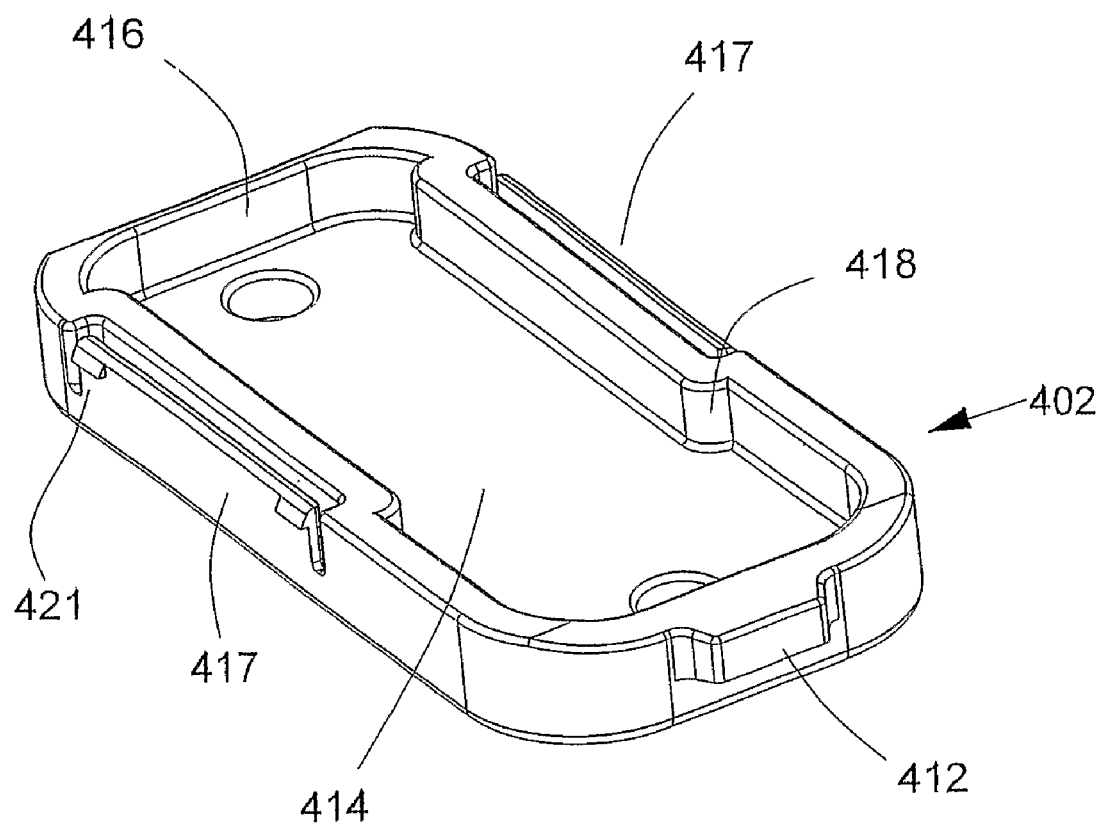
FIG. 16 is a perspective view of a shoe attachment element embodiment.
Figure 17:
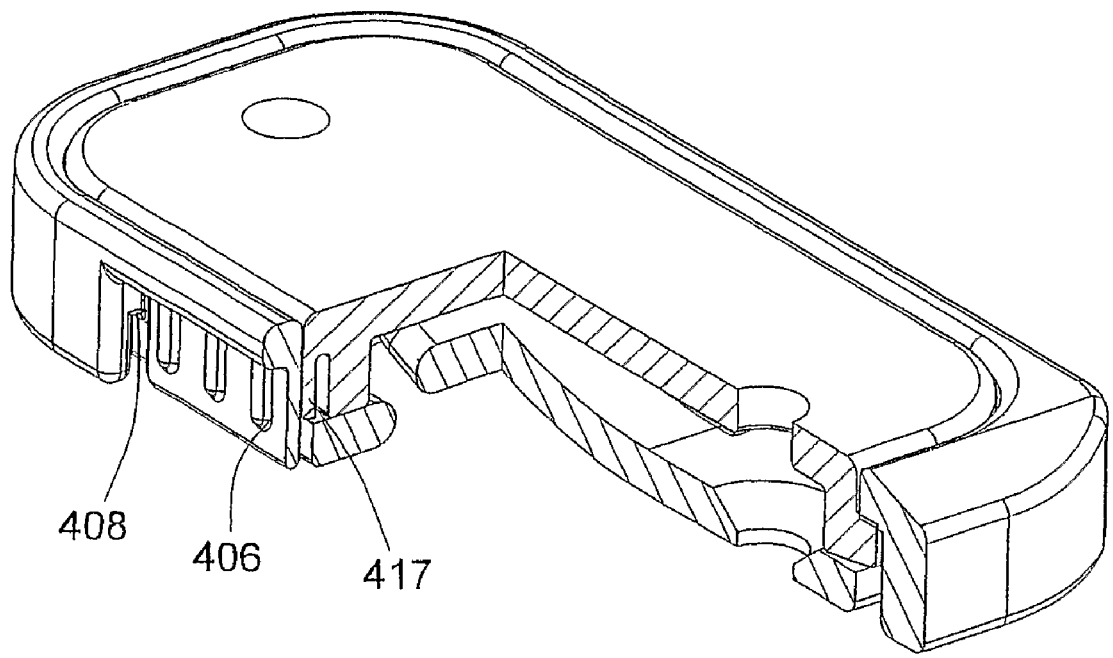
FIG. 17 is a partial cut-away view of a shoe releasing assembly with bar and shoe attachment members as shown in FIGS. 16 and 17.

Referring now to FIGS. 15 through 17, another embodiment of the releasing member of a shoe releasing assembly is described. Flexible attachment wall portions 417 projecting parallel to attachment member 402 wall 416 and positioned opposite each other and adjacent recessed wall areas 418 includes tabs 421 at the top of the wall portion 417 for engagement to corresponding locking elements 408. Upon engagement, tabs 421 and wall portions 417 are deflected to receive corresponding locking elements 408 of attachment member 401. At full engagement, tabs 421 and wall portions 417 project toward their initial position and tabs 421 engage locking elements 408 as show in FIG. 17. To disengage the attachment members, release members 406 are squeezed toward each other causing the flexible wall elements to deflect tabs 421 from locking elements 408 for quick release of the attachment members. In this arrangement, the user may be protected from being pinched by the close tolerance elements and/or disengaging tabs/locking elements.

Also depicted in FIG. 15 is tongue-like deflector 411, which is interfered with by base 414 of attachment member 402. Securing element 410 of attachment member 401 is provided for receiving protrusion element 412 of attachment member 402.

Figure 18:
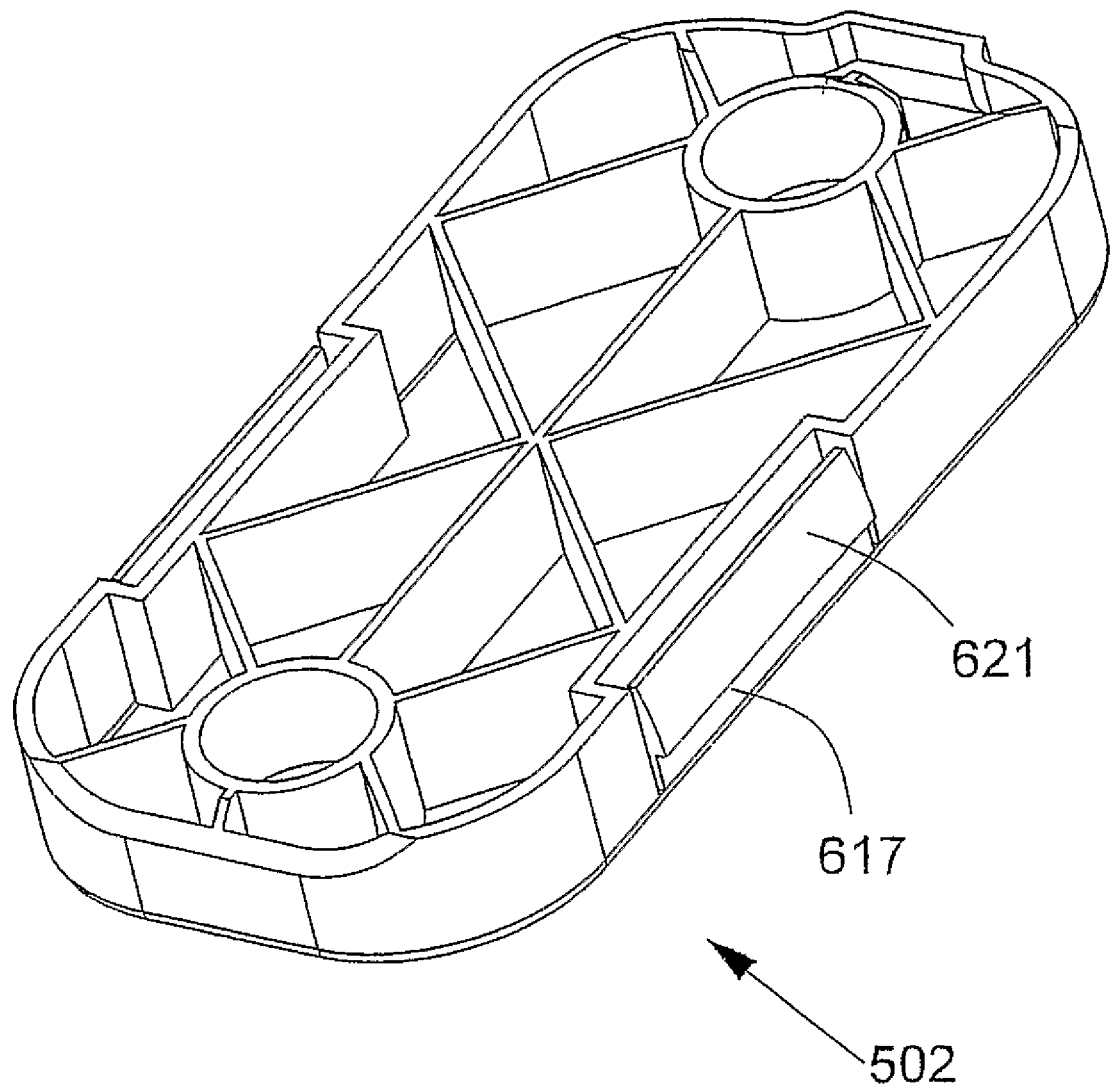
FIG. 18 is a perspective view of a shoe attachment member embodiment.

FIG. 18 depicts attachment member 502, which may reduce weight and/or improve structural strength to the assembly. Alternate retaining elements 621 attached to flexible wall portions 617 are shown.

The recess of the attachment member will receive the corresponding attachment member wall section and the heel and toe of the corresponding attachment member when it is vertically inclined into the recess. The recess may be designed to allow the heel or toe to rotate freely from the point where the heel or toe contacts the base, until the two components are fully engaged together. The recess may also extend through the base of the either attachment member to minimize or eliminate undercut, thus simplifying the injection molding procedure. The recess and corresponding wall section, and heel/toe contacts may be interchanged from being located on the bar and shoe attachment members, as desired.

Threaded inserts may snapped into the bar attachment member to firmly fix it to a bar or Dennis Browne Splint. The threaded press-fits will apply an interference fit into two holes molded into the base of the bar attachment. Attaching the threaded inserts may allow for an easily molded bar attachment surface, as well as a more robust thread for the screws adjoining the bar attachment and the splint.

Each attachment member component may be designed so that it can not be assembled incorrectly. By tapering the shape of each piece, the attachment member components may only be snap-fitted together in a correct alignment configuration with the ends of each attachment member component configured in the proper direction.

The attachment members may further comprise a heel-extension element 350 as shown in FIG. 14, which may be a small rectangular extension centered at one end of one of the attachment member that mates easily with a "heel-hole" of a corresponding attachment member. This feature may allow the surfaces to be easily mated together by inserting the heel-extension into a small "heel hole" in the one attachment member then rotating the shoe attachment along its vertical axis to lower the shoe attachment component into the corresponding attachment member. The heel may be chamfered on the underside so that the child's foot can come in at an angle and rest the toe on the base of an attachment member before sliding the toe into its corresponding hole. This heel-extension feature may be advantageous, for example, on a shoe attachment member when applying the Denis Browne splint while the infant is wearing the shoe. It may allow the caregiver to quickly and easily attach shoe attachment member into the bar attachment member without removing the shoe.

The actuator used to disassemble the parts may be located underneath the toe end of the shoe. When connected to standard shoes used with the Dennis Browne splint, the toe of the shoes will likely extend past the actuator used to disassemble the attachment members. This may provide protection from a child hitting the actuator and inadvertently disconnecting the attachment members. Walls of the attachment members also extend adjacent to the actuator to protect the sides thereof from inadvertent contact.

The assembly components may be made from various materials. The preferred material for the bar attachment and shoe attachment is a strong thermoplastic. The thermoplastic may be chosen based on impact and fatigue resistance, for example. Various polymer plastics, and metals, composites and mixtures thereof may be used. Both the bar and shoe attachments may be molded with a simple open and close mold by way of liquid injection or similar means. Preferably, neither attachment member component possesses undercuts, so molding may be both quick and easy.

The assembly described above will normally be supplied in disassembled form or as a kit. However, the term "assembly" as used herein is intended to include within its scope not only the elements of the assembly in disassembled form, but the elements thereof in assembled form as well.

Visible indicia comprising at least one symbol may be provided on the base of the either attachment member to assist in the proper placement of the member on the bar and/or insertion of the shoe attachment member.

The shoe attachment member may be secured to the soles of the patient's shoes, which may be either a pair of ordinary shoes, or special shoes if desired. Preferably, the shoe attachment members are attached to the soles of the shoe by adhesive, screws, rivets or other fastening means may be used alternatively if desired. The screws and inserts into which the screw is threaded are preferably metal. Likewise, the various other screws used in the appliance are preferably metal screws.

All of the foregoing steps involved in the initial installation may be accomplished by the physician in his own office or by the caregiver with appropriate instruction by a physician.

The shoe release assembly as herein described may be usable in a wide variety of devices other than the foot orthosis appliance described above.

Figure 19:
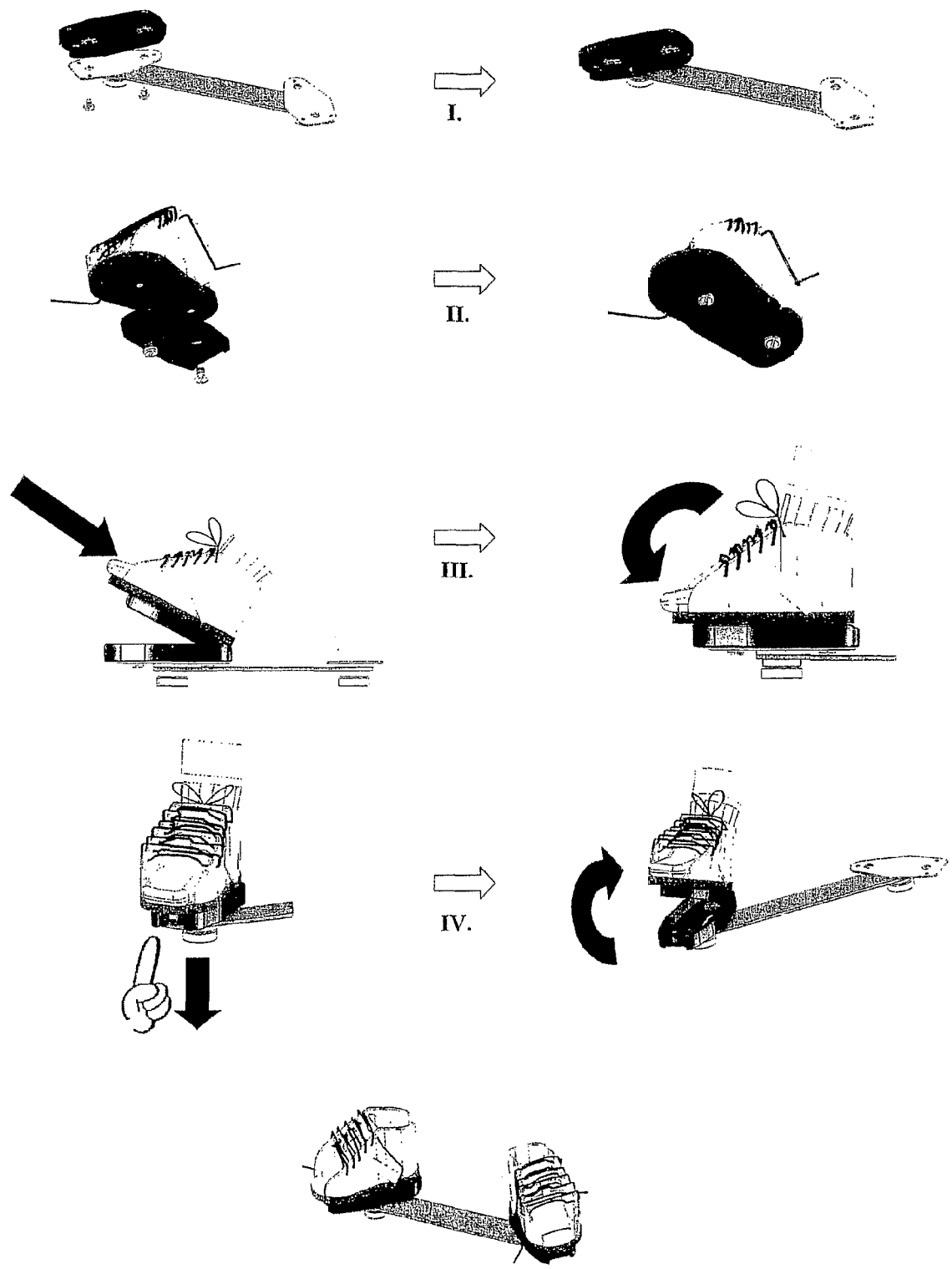
FIG. 19 is a schematic representation of the shoe releasing assembly.

FIG. 19 schematically depicts, by way of example, the assembly of the bar attachment member to the bar or splint as indicated by arrow I. Assembly of the shoe attachment member to the sole of a shoe is indicated by arrow II. Engagement of the shoe attachment member with the bar attachment member is indicated, for example, by vertically inclined heel-then-toe motion, by arrow III. Disengagement of the shoe and shoe attachment member is indicated by arrow IV. The assembled shoe releasing assembly 900 is represented in FIG. 19, by way of example, as would be intended for the use in treating a foot disorder in a subject in need thereof.

By reason of the fact that the structure includes a vertically inclined engagement, a patient's caregiver may easily remove and replace the shoe without disturbing the bar or splint setting, and may check the setting to be sure it is in accordance very easily. This facilitates ease of use for seating or otherwise positioning the patient or manipulating the shoes for any other reason.

The appliance described above is useful in the correction of a wide variety of common lower extremity deformities, including such conditions as acetabular dipsplasia, external tibial tortion, genu varum (bow legs), internal tibial tortion, metorasis odductus, talipes equinovarus (club foot), windswept deformities as well as various other less common conditions.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

While the invention has been described in detail and with reference to specific embodiments thereof, it will be apparent to one skilled in the art that various changes and modifications can be made without departing from the spirit and scope of the invention.

What is claimed is:

1. A shoe releasing assembly comprising:
   a bar attachment member securable to a bar or splint, the bar attachment member comprising a base having a forward end and a rearward end;
   a wall section at least partially surrounding the base and defining a recess;
   at least one releasing member integral to the bar attachment member and positioned within the recess or the wall section, the releasing member comprising at least one retaining element;
   a shoe attachment member securable to the sole of a shoe, the shoe attachment member comprising a shoe attachment base having a heel end and a toe end;
   a shoe attachment wall section at least partially surrounding the shoe attachment base and having a shape conforming to the recess of the bar attachment member for vertically inclined insertion into the recess of the bar attachment member;
   an integral locking element adjacent the shoe attachment wall for releasably engaging the retaining element;
   a protrusion element integral with the shoe attachment member and extending outwardly from either the heel end or the toe end; and
   a securing element integral with the bar attachment member and adjacent to the base, the securing element positioned either at the forward end or the rearward end such that the securing element cooperatively engages a corresponding heel or toe end protrusion element to secure the shoe attachment member to the bar attachment,
   wherein the releasing member provides for disengagement of the retaining element from the integral locking element.

2. The shoe releasing assembly of claim 1, wherein the at least one releasing member is positioned at the forward or rearward end of the bar attachment member.

3. The shoe releasing assembly of claim 1, wherein the at least one releasing member is positioned between the forward or rearward end of the bar attachment member.

4. The shoe releasing assembly of claim 1, wherein the protrusion element is positioned at the heel end of the shoe attachment member.

5. The shoe releasing assembly of claim 1, wherein the securing element is positioned at the rearward end of the bar attachment member.

6. The shoe releasing assembly of claim 1, wherein the protrusion element of the shoe attachment member is positioned such that the releasing member of the bar attachment is opposite thereof upon assembly.

7. A shoe releasing assembly comprising:
   a bar attachment member securable to a bar or splint, the bar attachment member comprising a base having a forward end and a rearward end;
   a wall section at least partially surrounding the base;
   an integral locking element adjacent the wall section;
   a shoe attachment member adapted to be secured to the sole of a shoe, the shoe attachment member comprising a shoe attachment base having a heel end and a toe end;
   a shoe attachment wall section at least partially surrounding the shoe attachment base and defining a recess, the recess having a shape conforming to the wall section of the bar attachment member for vertically inclined insertion of the wall section of the bar attachment member into the recess of the shoe attachment member;

at least one releasing member integral to the shoe attachment member positioned within the recess or shoe attachment wall section, the releasing member comprising a retaining element for releasably engaging with the locking element;

a protrusion element integral with the bar attachment member and extending inwardly from the wall and positioned at either the forward end or rearward end; and a securing element integral with the shoe attachment member and positioned at either the heel end or the toe end such that the securing element cooperatively engages a corresponding forward or reward end protrusion element to secure the shoe attachment member to the bar attachment, wherein the releasing member provides for disengagement of the retaining element from the locking element.

8. The shoe releasing assembly of claim 7, wherein the at least one releasing member is positioned at the heel or toe end of the shoe attachment member.

9. The shoe releasing assembly of claim 7, wherein the at least one releasing member is positioned between the heel or toe end of the shoe attachment member.

10. The shoe releasing assembly of claim 7, wherein the protrusion element is positioned at the bar attachment member.

11. The shoe releasing assembly of claim 7, wherein the securing element is positioned at the rearward end of the heel end of the shoe attachment member.

12. A shoe releasing assembly comprising:
a bar attachment member securable to a bar or splint, the bar attachment member comprising a base having a forward end and a rearward end;
a wall section at least partially surrounding the base and defining a recess;
at least one releasing member integral to the bar attachment member and positioned within the recess or the wall section, the releasing member comprising at least one retaining element, wherein the at least one releasing member is positioned at the forward or rearward end of the bar attachment member; and
a securing element integral with the bar attachment member and adjacent to the base, the securing element positioned either at the forward end or the rearward end such that the securing element cooperatively engages a corresponding heel or toe end protrusion element of a corresponding shoe attachment member; and
a shoe attachment member securable to the sole of a shoe, the shoe attachment member comprising a shoe attachment base having a heel end and a toe end;
a shoe attachment wall section at least partially surrounding the shoe attachment base and having a shape conforming to the recess of the bar attachment member for vertically inclined insertion into the recess of the bar attachment member;
an integral locking element adjacent the shoe attachment wall for releasably engaging the retaining element; and
a protrusion clement integral with the shoe attachment member and extending outwardly from either the heel end or the toe end for engagement with the securing element of the bar attachment member;
wherein the releasing member provides for disengagement of the retaining element from the integral locking element.

13. A shoe releasing assembly comprising:
a bar attachment member securable to a bar or splint, the bar attachment' member comprising a base having a forward end and a rearward end;
a wall section at least partially surrounding the base;
an integral locking element adjacent the wall section; and
a protrusion element integral with the bar attachment member and extending outwardly from either the forward end or the reward end for engagement with a corresponding securing element of a shoe attachment member; and
a shoe attachment member adapted to be secured to the sole of a shoe, the shoe attachment member comprising a shoe attachment base having a heel end and a toe end;
a shoe attachment wall section at least partially surrounding the shoe attachment base and defining a recess, the recess having a shape conforming to the wall section of the bar attachment member for vertically inclined insertion of the wall section of the bar attachment member into the recess of the shoe attachment member;
at least one releasing member integral to the shoe attachment member positioned within the recess or shoe attachment wall section, the releasing member comprising a retaining element for releasably engaging with the locking element, wherein the at least one releasing member is positioned at the heel end or toe end of the shoe attachment member; and
a securing element integral with the shoe attachment member and adjacent to the shoe attachment base, the securing element positioned either at the heel end or the toe end such that the securing element cooperatively engages the forward end or rearward end protrusion element to secure the shoe attachment member to the bar attachment;
wherein the releasing member provides for disengagement of the retaining element from the locking element.

14. A shoe releasing assembly comprising:
a bar attachment member securable to a bar or splint, the bar attachment member comprising a base having a forward end and a rearward end;
a wall section at least partially surrounding the base and defining a recess; and
at least one releasing member integral to the bar attachment member and positioned within the recess or the wall section, the releasing member comprising at least one retaining element;
a shoe attachment member securable to the sole of a shoe, the shoe attachment member comprising a shoe attachment base having a heel end and a toe end;
a shoe attachment wall section at least partially surrounding the shoe attachment base and having a shape conforming to the recess of the bar attachment member for vertically inclined insertion into the recess of the bar attachment member;
a interference element extending at least partially upwardly from the base of the bar attachment member, wherein the interference element provides a stored force upon engagement, the stored force capable of assisting release of the shoe attaching member from the bar attachment member; and
an integral locking element adjacent the shoe attachment wall for releasably engaging the retaining element;
wherein the releasing member provides for disengagement of the retaining element from the integral locking element.

15. The shoe releasing assembly of claim 14, wherein the interference element provides a reduction of movement of the shoe attachment member upon engagement with the bar attachment member.

16. The shoe releasing assembly of claim 14, wherein the shoe attaching member further comprises a deflector to engage the interference element.

17. A shoe releasing assembly comprising:
a bar attachment member securable to a bar or splint, the bar attachment member comprising a base having a forward end and a rearward end;
a wall section at least partially surrounding the base; and
an integral locking element adjacent the wall section;
a shoe attachment member adapted to be secured to the sole of a shoe, the shoe attachment member comprising a shoe attachment base having a heel end and a toe end;
a shoe attachment wall section at least partially surrounding the shoe attachment base and defining a recess, the recess having a shape conforming to the wall section of the bar attachment member for vertically inclined insertion of the wall section of the bar attachment member into the recess of the shoe attachment member;
a interference element extending at least partially upwardly from the base of the bar attachment member, wherein the interference element provides a stored force upon engagement, the stored force capable of assisting release of the shoe attaching member from the bar attachment member; and
at least one releasing member integral to the shoe attachment member positioned within the recess or shoe attachment wall section, the releasing member comprising a retaining element for releasably engaging with the locking element;
wherein the releasing member provides for disengagement of the retaining element from the locking element.

18. The shoe releasing assembly of claim 17, wherein the interference element provides for a reduction of movement of the shoe attachment member upon engagement with the bar attachment member.

19. The shoe releasing assembly of claim 17, wherein the shoe attaching member further comprises a deflector adapted to engage the interference element.

20. A method for treating a foot disorder in a subject in need thereof, the method comprising
providing a shoe releasing assembly comprising
a bar attachment member securable to a bar or splint, the bar attachment member comprising a base having a forward end and a rearward end;
a wall section at least partially surrounding the base and defining a recess;
at least one releasing member integral to the bar attachment member and positioned within the recess or the wall section, the releasing member comprising at least one retaining element, wherein the at least one releasing member is positioned at the forward or rearward end of the bar attachment member; and
a securing element integral with the bar attachment member and adjacent to the base, the securing element positioned either at the forward end or the rearward end such that the securing element cooperatively engages a corresponding heel or toe end protrusion element of a corresponding shoe attachment member; and
a shoe attachment member securable to the sole of a shoe, the shoe attachment member comprising a shoe attachment base having a heel end and a toe end;
a shoe attachment wall section at least partially surrounding the shoe attachment base and having a shape conforming to the recess of the bar attachment member for vertically inclined insertion into the recess of the bar attachment member;
an integral locking element adjacent the shoe attachment wall for releasably engaging the retaining element; and
a protrusion element integral with the shoe attachment member and extending outwardly from either the heel end or the toe end for engagement with the securing element of the bar attachment member;
wherein the releasing member provides for disengagement of the retaining element from the integral locking element,
wherein the shoe attachment member is attachable to the sole of a shoe of a subject in need of treatment of a foot disorder.

21. The method of claim 20, wherein the foot disorder is acetabular dipsplasia, external tibial tortion, genu varum (bow legs), internal tibial tortion, metorasis odductus, talipes equinovarus (club foot), or windswept deformities.

22. A method for treating a foot disorder in a subject in need thereof, the method comprising
providing a shoe releasing assembly comprising
a bar attachment member securable to a bar or splint, the bar attachment' member comprising a base having a forward end and a rearward end;
a wall section at least partially surrounding the base;
an integral locking element adjacent the wall section; and
a protrusion element integral with the bar attachment member and extending outwardly from either the forward end or the reward end for engagement with a corresponding securing element of a shoe attachment member; and
a shoe attachment member adapted to be secured to the sole of a shoe, the shoe attachment member comprising a shoe attachment base having a heel end and a toe end;
a shoe attachment wall section at least partially surrounding the shoe attachment base and defining a recess, the recess having a shape conforming to the wall section of the bar attachment member for vertically inclined insertion of the wall section of the bar attachment member into the recess of the shoe attachment member;
at least one releasing member integral to the shoe attachment member positioned within the recess or shoe attachment wall section, the releasing member comprising a retaining element for releasably engaging with the locking element, wherein the at least one releasing member is positioned at the heel end or toe end of the shoe attachment member; and
a securing element integral with the shoe attachment member and adjacent to the shoe attachment base, the securing element positioned either at the heel end or the toe end such that the securing element cooperatively engages the forward end or rearward end protrusion element to secure the shoe attachment member to the bar attachment;
wherein the releasing member provides for disengagement of the retaining element from the locking element;
wherein the shoe attachment member is attachable to the sole of a shoe of a subject in need of treatment of a foot disorder.

23. The method of claim 22, wherein the foot disorder is acetabular dipsplasia, external tibial tortion, genu varum (bow legs), internal tibial tortion, metorasis odductus, talipes equinovarus (club foot), or windswept deformities.

* * * * *